United States Patent [19]
Campbell et al.

[11] Patent Number: 5,242,801
[45] Date of Patent: Sep. 7, 1993

[54] DIAGNOSING MALIGNANT HYPERTHERMIA SUSCEPTIBILITY BY DETECTION OF ABNORMAL PROTEOLYTIC ENZYME DIGESTION FRAGMENTS OF THE RYANODINE RECEPTOR

[75] Inventors: Kevin P. Campbell; C. Michael Knudson; Steven D. Kahl, all of Iowa City, Iowa; Charles F. Louis; James R. Mickelson, both of St. Paul, Minn.

[73] Assignees: University of Iowa Research Foundation, Iowa, Iowa; Regents of the University of Minnesota, Minneapolis, Minn.

[21] Appl. No.: 562,719

[22] Filed: Aug. 6, 1990

[51] Int. Cl.$^5$ .................. C12Q 1/00; C12Q 1/37; G01N 33/53; G01N 33/544
[52] U.S. Cl. ..................... 435/7.2; 435/24; 436/530; 436/63; 530/387.1
[58] Field of Search ............ 435/172.2, 2, 7.2, 24; 530/387, 387.1; 514/103, 374; 250/361; 436/63, 530

[56] References Cited

U.S. PATENT DOCUMENTS

| | | | |
|---|---|---|---|
| 4,452,901 | 6/1984 | Gordon et al. | 436/506 |
| 4,837,163 | 6/1989 | Ohnishi | 436/63 |
| 4,912,202 | 3/1990 | Campbell et al. | 530/387 |

OTHER PUBLICATIONS

White et al (1986) Medical Virology, Academic Press Orlando, pp. 330-333.
Tsang et al. (1983) Enzyme Linked Immunoelectrotransfer Blot Techniques (EITB) for Studying the Specificities of Antigens and Antibodies Separated by Gel Electrophoresis. Methods in Enzymol. 92:377-391.
Lin et al (1986) Sequential Detection of Different Antigens Induced by Epetein Barr Virus and HSV in the Same Western Using Dual Antibody Probes J. Virol 59:522-4.
Campbell et al., *J. Biol. Chem.*, 262(14): 6460-6463 (1987).
Imagawa et al., *J. Biol. Chem.*, 262(34): 16636-16643 (1987).
Inui et al., *J. Biol. Chem.*, 262(4): 1740-1747 (1987).
Lai et al., *Nature*, 331: 315-319 (1988).
Mickelson et al., *J. Biol. Chm.*, 263(19): 9310-9315 (1988).
Meissner et al., *J. Biol. Chem.*, 264(3): 1715-1722 (1989).
MacLennan et al., *Nature*, 343: 559-561 (1990).
Knudson et al., *J. Biol. Chem.*, 264(5): 2421-2424 (1990).

*Primary Examiner*—Christine M. Nucker
*Assistant Examiner*—D. R. Preston
*Attorney, Agent, or Firm*—Hamilton, Brook, Smith & Reynolds

[57] ABSTRACT

The present invention relates to a method of diagnosing malignant hyperthermia susceptibility by detecting abnormal ryanodine receptor fragments following proteolytic enzyme digestion of ryanodine receptors isolated from the sarcoplasmic reticulum of mammalian skeletal muscle. The detection of abnormal ryanodine receptor fragments is indicative of malignant hyperthermia susceptibility.

3 Claims, 5 Drawing Sheets

DIAGNOSING MALIGNANT HYPERTHERMIA SUSCEPTIBILITY BY DETECTION OF ABNORMAL PROTEOLYTIC ENZYME DIGESTION FRAGMENTS OF THE RYANODINE RECEPTOR

GOVERNMENT SUPPORT

Work described herein was supported by Grants [#] 39265 and GM-31382 from the National Institutes of Health.

BACKGROUND OF THE INVENTION

Malignant hyperthermia is an inherited skeletal muscle disorder of humans and pigs. The disease is characterized by an accelerated muscle metabolism, contracture development, and rapidly rising temperature in response to certain halogenated anesthetics. Once initiated, a vicious cycle is established and a fulminant syndrome evolves in which the body temperature may exceed 109° F. The clinical picture is generally accompanied by muscle rigidity, tachychardia and other signs of circulatory and metabolic stress. The syndrome may progress directly to rigor and death from cardiovascular stress unless the malignant hyperthermia episode is recognized and treated promptly with the skeletal muscle relaxant, dantrolene. The reported incidence of malignant hyperthermia ranges from approximately 1 per 10,000 to 1 per 50,000 anesthetics, with an apparently higher incidence in children.

In addition to triggering malignant hyperthermia by halothane anesthetic, porcine malignant hyperthermia is also consistently triggered by excitement, apprehension, exercise, or environmental stress such as heat or hypoxia. Episodes of malignant hyperthermia in pigs yield inferior, pale, soft and exudative pork.

Active malignant hyperthermia results in a dramatic elevation of intracellular calcium in skeletal muscle fibers. The exact cause of the explosive rise in sarcoplasmic calcium is not completely understood. Several laboratories, however, have found that calcium release from malignant hyperthermia susceptible sarcoplasmic reticulum in skeletal muscle differs from that of normal sarcoplasmic reticulum in both isolated vesicles, as well as intact and skinned fibers. Consequently, the calcium release channel of the sarcoplasmic reticulum has been suspected of playing a significant role in malignant hyperthermia.

Evaluation of malignant hyperthermia susceptibility includes a history and physical examination for detection of subclinical symptoms. A geneology going back two generations with specific information about anesthetic exposure and agents will estimate the likelihood of exposure to triggering agents. Predisposition to the disease is also currently determined experimentally through a halothane and caffeine-induced contracture test on a skeletal muscle biopsy. This method, however, is time consuming, labor intensive and not always conclusive. A large biopsy sample is needed, the patient must be greater than 60 pounds for biopsy and the biopsy sample must be fresh. A quick, simple and accurate test for this disease would be immensely useful to physicians in identifying patients with susceptibility to malignant hyperthermia. The method would also provide swine breeders with a means of identifying animals susceptible to malignant hyperthermia attacks induced by stress before slaughter.

SUMMARY OF THE INVENTION

The present invention relates to a method of diagnosing malignant hyperthermia by detecting abnormal ryanodine receptor fragments following proteolytic enzyme digestion of ryanodine receptors isolated from the sarcoplasmic reticulum of mammalian skeletal muscle. The detection of abnormal ryanodine receptor fragments is indicative of malignant hyperthermia.

Monoclonal and polyclonal antibodies specific for the ryanodine receptor and ryanodine receptor fragments are particularly useful in this invention. For example, these antibodies can be labeled and used for binding the ryanodine receptor fragments, thereby allowing detection of said fragments.

The current technology for detection and diagnosis of malignant hyperthermia involves a functional test on skeletal muscle biopsies. The test is time consuming, labor intensive and not always conclusive. The present invention overcomes the limitations of the current technology by not relying on a functional assay to detect malignant hyperthermia from skeletal muscle biopsies. In addition, the invention can utilize biopsy samples obtained by needle and frozen biopsy samples which can allow long-time storage before testing. The invention provides a quick and accurate means of identifying a structural difference in the ryanodine receptor of skeletal muscle from normal and malignant hyperthermia susceptible mammals.

DETAILED DESCRIPTION OF THE INVENTION

Figure 1:
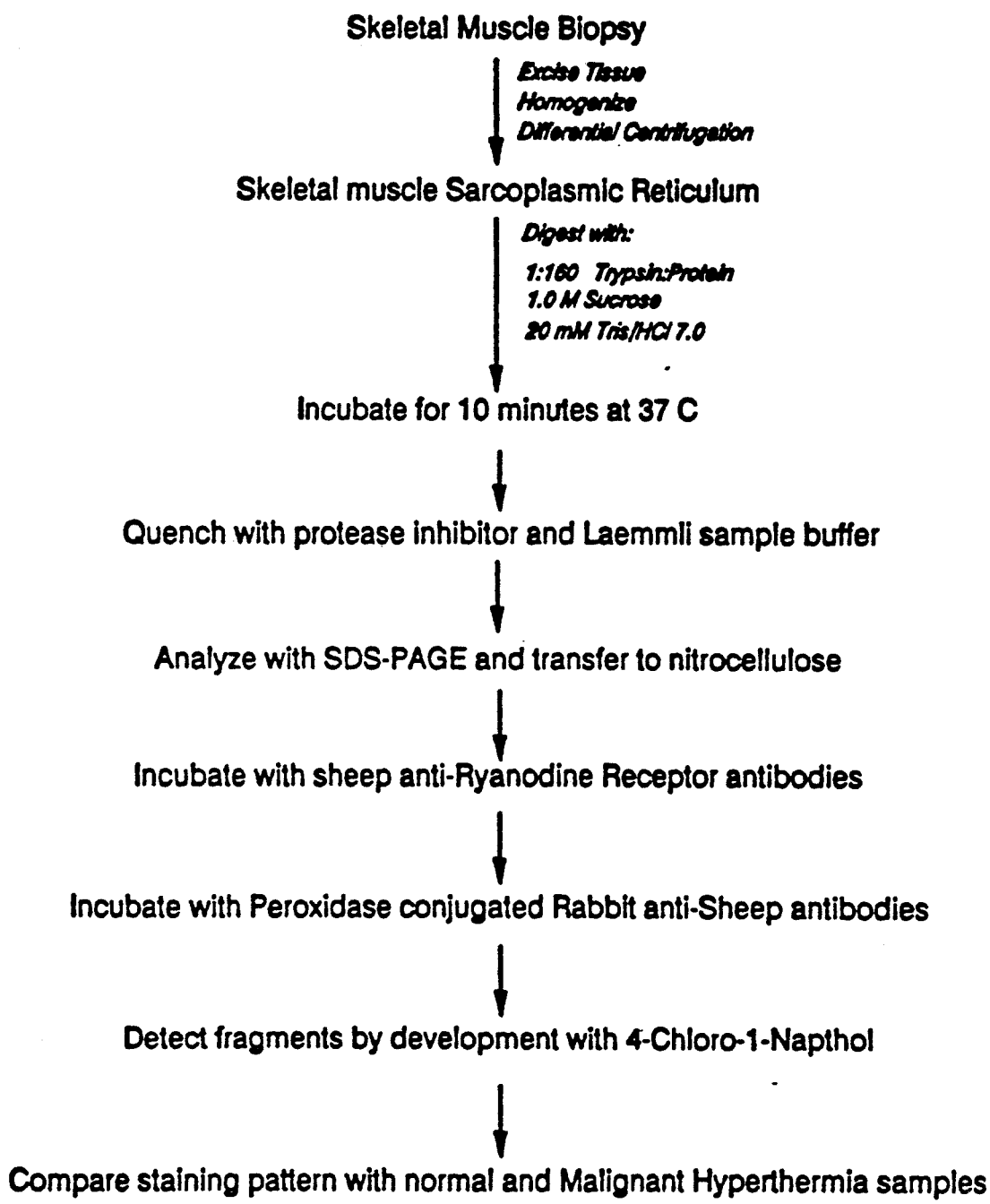
FIG. 1 is a flow diagram of the steps comprising the method of immunoblot analysis for ryanodine receptor fragments prepared from mammalian skeletal muscle biopsies.

The ryanodine receptor is a calcium release channel in skeletal muscle fibers. The receptor is membrane bound in the sarcoplasmic reticulum which is a sheath of anastomosing, flattened membranes derived from the endoplasmic reticulum, which surrounds each myofibril in a muscle. The ryanodine receptor of the sarcoplasmic reticulum has been shown to be the calcium release channel responsible for the initiation of calcium release from the sarcoplasmic reticulum in skeletal muscle. This invention is based, in part, on the discovery that when a receptor of the sarcoplasmic reticulum from malignant hyperthermia susceptible and normal skeletal muscle is isolated and digested with the enzyme, trypsin, an approximate 86 kDa ryanodine receptor peptide is the predominant fragment in normal sarcoplasmic reticulum while an approximate 99 kDa ryanodine receptor peptide fragment is the major ryanodine receptor peptide detected in malignant hyperthermia susceptible sarcoplasmic reticulum. A preferred embodiment of this invention relates to a method of identifying and detecting ryanodine receptor fragments from mammalian skeletal muscle biopsies using antibodies to the ryanodine receptor which react to the ryanodine receptor and enzyme digested fragments of the ryanodine receptor from mammalian skeletal muscle sarcoplasmic reticulum. Determination of the presence of an abnormal enzyme digested fragment of the ryanodine receptor or an abnormal ratio of one digested fragment to other digested fragments is indicative of susceptibility to malignant hyperthermia.

Monoclonal and polyclonal antibodies specific for the ryanodine receptor and enzyme-digested fragments of the ryanodine receptor are particularly useful in the diagnostic method of this invention. Monoclonal antibodies useful in this invention can be obtained by employing well-known methods to produce hybridomas. Thus, an animal is immunized with a preparation containing the ryanodine receptor. A fused cell hybrid is then formed between antibody-producing cells from the immunized animal and an immortilizing cell such as a myeloma.

In preferred embodiments anti-ryanodine receptor monoclonal antibodies of this invention are produced by murine hybridomas formed by fusion of: a) mouse myeloma or hybridoma which does not secrete antibody with b) murine spleen cell which secrete antibodies obtained from mice immunized against the ryanodine receptor.

Typically, the mice are immunized with a primary injection of the ryanodine receptor followed by a number of boosting injections of the ryanodine receptor. During or after the immunization procedure, sera of the mice may be screened to identify those mice in which a substantial immune response to the complex has been evoked. From selected mice, the spleen cells are obtained and fusions are performed. Suitable fusion techniques are the Sendai virus technique (Kohler, G. and Milstein, C., *Nature*, 256: 495 (1975)), or the polyethyleneglycol method (Kennet, R. H., "Monoclonal Antibodies, Hybridomas—A New Dimension in Biological Analysis," Ed. R. H. Kennet, T. McKern and K. B. Bechtol, Plenum Press, N.Y. (1980)), hereby incorporated by reference.

The hybridomas are then screened for production of anti-ryanodine receptor antibodies. A suitable screening technique is a solid phase radioimmunoassay. A solid phase immunoadsorbant is prepared by coupling ryanodine receptors or ryanodine receptor fragments to an insoluble matrix. The immunoadsorbant is brought into contact with culture supernatants of hybridomas. After a period of incubation, the solid phase is separated from the supernatants, then contacted with a labeled antibody against murine immunoglobulin. Label associated with the immunoadsorbant indicates the presence of hybridoma products reactive with ryanodine receptors or ryanodine receptor enzyme-digested fragments. The hybridoma products are then examined for their ability to react with natural and synthetic components of the ryanodine receptor.

The monoclonal anti-ryanodine receptor antibodies can be produced in large quantities by injecting anti-ryanodine receptor antibody producing hybridoma cells into the peritoneal cavity of mice and, after an appropriate time, harvesting acites fluid from the mice which yield a high titer of homogeneous antibody. The monoclonal antibodies are isolated therefrom. Alternatively, the antibodies can be produced by culturing anti-ryanodine receptor antibody producing cells in vitro and isolating secreted monoclonal anti-ryanodine receptor antibodies from the cell culture medium directly.

Another method of forming antibody producing cells is by viral or oncogenic transformation. For example, a B-lymphocyte which produced a ryanodine receptor specific antibody may be infected and transformed with a virus, such as the Epstein-Barr virus, to give an immortal antibody producing cell. See Kozbon and Roder, *Immunology Today*, 4(3):72-79 (1983), hereby incorporated by reference. Alternatively, the B-lymphocyte may be transformed by a transforming gene or gene product.

Polyclonal antibodies can be prepared by immunizing an animal with a purifed preparation of the ryanodine receptor or preparations containing enzyme-digested fragments of the ryanodine receptor. The animal is maintained under conditions whereby antibodies reactive with the ryanodine receptor or fragments of the ryanodine receptor are produced. Blood is collected from the animal upon reaching a desired titer of antibodies. The serum containing the polyclonal antibodies (antisera) is separated from other blood components. The polyclonal antibody containing serum can optionally be further separated into fractions of particular types of antibodies (e.g., IgG or IgM).

In a preferred embodiment of the diagnostic method of this invention, a muscle biopsy sample is treated in a procedure which isolates the sarcoplasmic reticulum and renders the ryanodine receptors of the sample susceptible to partial proteolysis with an enzyme. The cleavage products are treated with sodium dodecyl sulfate and separated by polyacrylamide gel electrophoresis. The fragments are then reacted with antibodies specific for the ryanodine receptor. The pattern of peptide fragments produced is characteristic of the protein substrate (ryanodine receptors), the proteolytic enzyme and the specific antibodies used. The patterns developed from malignant hyperthermia susceptible and normal samples are compared.

Muscle samples can be obtained from patients and animals by surgical biopsy or needle biopsy. The site of biopsy could be any skeletal muscle. The amount of muscle obtained should be enough to detect the trypsin-digested fragments of the ryanodine receptor by the diagnostic method described within this application.

Preparation of heavy sarcoplasmic reticulum can be isolated from the biopsy sample by the methods of Mickelson, J. R., et al., *Biochem. Biophys. Acta*, 862: 318-328 (1986) and Mickelson, J. R., et al., *J. of Biol. Chem.*, 263: 9310-9315 (1988), hereby incorporated by reference. The isolated sarcoplasmic reticulum preparations are then digested with a protease or proteolytic enzyme. In a preferred embodiment, this enzyme is trypsin which is a specific protease that cleaves peptide bonds on the C-terminal side of arginine and lysine residues. These amino acids are relatively abundant in most proteins, accounting for approximately 11.5% of the total amino acids in an average protein. The concentration of proteolytic enzyme, the length in time of digestion, and the temperature at which the digestion occurs can all vary depending upon the desired degree of digestion required to observe the appearance of abnormal fragments or an abnormal ratio of fragments indicative of malignant hyperthermia susceptible and normal muscle samples. The digestion is ended by the addition of protease inhibitors such as phenylmethylsulfonyl fluoride and by dilution with a buffer. The proteolytic enzyme digested sample is then prepared for electrophoresis by treatment with sodium dodecyl sulfate (SDS).

The SDS treated sample is then electrophoresed, for example, by polyacrylamide gel electrophoresis (PAGE). The sample is introduced into the electrophoretic system at the stacking gel. With an electric field applied, ions move toward electrodes, but at the pH prevailing in the stacking gel, the protein-SDS complexes have mobilities intermediate between chloride ions (present throughout the system) and glycinate ions (present in the reservoir buffer). The chloride ions have the greatest mobility. The following larger ions concentrate into narrow zones in the stacking gel, but are not effectively separated there. When the moving zones reach the separating gel, their respective mobilities change in the pH prevailing there and the glycinate ions front overtakes the protein-SDS complex zones to leave them in a uniformly buffered electric field to separate from each other according to size and charge. Since protein (or rather their complexes with SDS) are resolved largely on the basis of differences in their sizes, electrophoretic mobility in SDS gels may be used to estimate the molecular weight of a protein by comparison of proteins of known size.

Following separation by SDS-PAGE, the separated fragments of the enzyme digested ryanodine receptors are transferred from the gel matrix to another support. The fragments are transferred out of the gel and onto a filter or membrane, forming an exact replica of the original protein separation, but leaving the transferred proteins accessible for further study. This transfer is known as protein blotting. There are two common methods for blotting, electroblotting and passive diffusion blotting. The support matrixes that can be used in the transfer include nitrocellulose filters, nylon filters, diazo papers, diethylaminoethyl (DEAE), anion exchange papers and membranes. The detection of transferred proteins can be accomplished by the use of the general protein dyes such as Amido black or Coomassie brilliant blue. In the preferred embodiment of this invention, antibodies which are specific for the ryanodine receptor or ryanodine receptor fragments can be used to bind to the various components. The complexes of antibodies and ryanodine receptor fragments can be detected with labeled antibodies. The levels of detection between normal samples and samples suspected of being extracted from muscle affected by malignant hyperthermia are compared. Detection of abnormal receptor fragments or an abnormal ratio of fragments following enzymatic digestion of the ryanodine receptors isolated from the sarcoplasmic reticulum of mammalian skeletal muscle is indicative of malignant hyperthermia susceptibility. For example, when trypsin is used to digest ryanodine receptors isolated from the sarcoplasmic reticulum of murine skeletal muscle, an abnormal ratio in the amount of 99 kDa ryanodine receptor fragment to 86 kDa ryanodine receptor fragment occurs and is indicative of malignant hyperthermia. The size of the fragments indicative of malignant hyperthermia can vary depending on the enzyme used for digestion and the species of mammal from which the digested ryanodine receptors were obtained.

The antibodies of the present invention can also be used in an enzyme-linked immunosorbant assay (ELISA) for detecting and quantifying peptide fragments from proteolytic enzyme-digested membrane fractions of mammalian skeletal muscle. Antibodies against peptide fragments to be measured are adsorbed to a solid support, in most cases a polystyrene microfilter plate. After coating the support and washing, a solubilized, trypsin-digested membrane fraction of skeletal muscle is added. If peptide fragments are present for which the antibodies are specific, they will bind to the adsorbed antibodies. Next, a conjugate that will also bind to the same peptide fragments is added. Conjugates are secondary antibody molecules to which an enzyme is covalently bound. After addition of a chromogenic substrate for the enzyme, the intensity of the colored reaction products generated will be proportional to the amount of conjugated enzyme and this indirectly to the amount of bound peptide fragment. Since the intensity of the developed color is proportional to the amount of peptide fragment present, determination of the color produced by a standard series of peptide fragment concentrations will allow the calculation of the amount of peptide fragments in an unknown sample. Many variations of this assay exist as described in Voller, A., Bidwell, D. E. and Bartlett, A., The Enzyme Linked Immunosorbent Assay (ELISA): A guide with abstracts of microplate applications, Dynatech Laboratories, Alexandria, Va. (1979) and are hereby incorporated by reference.

The invention is now further and specifically illustrated by the following examples. All parts and percentages are by weight unless otherwise specified.

EXAMPLE I

Immunoblot of malignant hyperthermia susceptible and normal sarcoplasmic reticulum digested with protease The teachings of all scientific publications cited in all examples herein are hereby incorporated by reference.

Malignant hyperthermia susceptible pigs (homozygous for halothane sensitivity) and normal Yorkshire (homozygous for the normal allele) pigs (60–100 pounds) from the University of Minnesota experimental farm were evaluated for malignant hyperthermia susceptibility by a halothane challange test 3–4 weeks before use. Heavy sarcoplasmic reticulum was isolated as described by the methods of Mickelson, J. R., supra, and Mickelson, J. R., et al., supra. Isolated heavy sarcoplasmic reticulum was diluted with buffer A (0.3M sucrose, 20 mM Tris-HCl, pH 7.4) and centrifuged for 30 minutes at 1OOK×G to remove protease inhibitors. The sarcoplasmic reticulum pellet was resuspended in buffer A, frozen in liquid nitrogen, and stored at $-135°$ C. until use sarcoplasmic reticulum (1 mg/ml) was digested with protease at 30° or 37° C. for various times in a buffer containing 1.0M sucrose and 20 mM Tris-HCl, pH 7.0. Digestion was inhibited by the addition of 1 mM phenylmethylsulfonyl fluoride followed by an equal volume of Laemmli sample buffer containing 6% sodium dodecyl sulfate and 2% 2-mercapto-ethanol.

Skeletal muscle membranes were analyzed by sodium dodecyl sulfate-polyacrylamide gel electrophoresis, SDS-PAGE, (3–12 or 5–16% gradient gels) using the buffer system of Laemmli and transferred to nitrocellulose membranes according to the method of Towbin et al., *Proc. Natl. Acad. Sci. USA,* 76: 4350–4354 (1979). The nitrocellulose blots were blocked for 1 hour with phosphate buffered saline (154 mM sodium chloride, 50 mM $NaH_2PO_4$, pH 7.4 with NaOH) containing 5% nonfat dry milk and subsequently incubated with primary antibody in Tris buffered saline (200 mM sodium chloride, 20 mM Tris-HCL, pH 7.5) containing 3% bovine serum albumin overnight at 4° C. Immunoblots were then washed three times with Tris buffered saline, incubated for 1 hour with secondary anti-IgG antibodies covalently linked to horseradish peroxidase in Tris buffered saline containing 3% bovine serum albumin, washed with Tris buffered saline and finally developed using 4-chloro-1-naphthol as the substrate.

Polyclonal antibodies against the sarcoplasmic reticulum calcium release channel were prepared by injection of a sheep with 0.5 mg of purified calcium release channel in 5 ml of Freud's complete adjuvant. The sheep was boosted 2 and 6 weeks later with another 0.5 mg of purified calcium release channel protein in 5 ml of Freud's incomplete adjuvant. Between 3 and 10 weeks later, blood was collected, incubated first at 37° C. for one hour and then at 4° C. overnight. The serum was collected by centrifugation, then tested for specificity and titered using immunoblots containing both purified calcium release channel and crude membranes.

Figure 2:
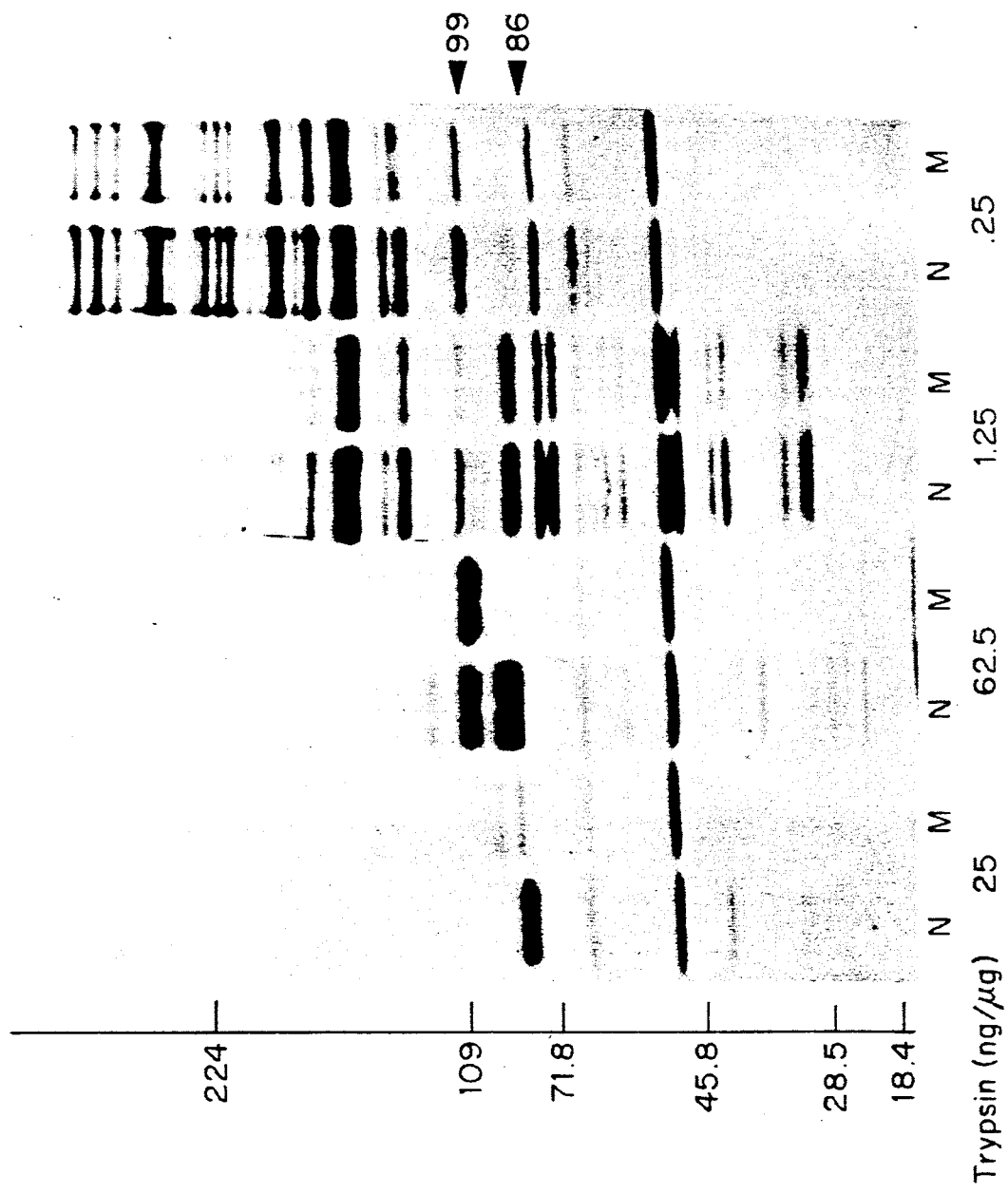
FIG. 2 is an immunoblot of malignant hyperthermia susceptible and normal sarcoplasmic reticulum digested with various concentrations of trypsin.

To explore potential differences in the structure of the malignant hyperthermia susceptible and normal calcium release channel or skeletal muscle, heavy sarcoplasmic reticulum vesicles were treated with various proteases and examined for differences in the pattern of proteolytic digestion. When samples were analyzed by Coomassie blue or silver staining of SDS-PAGE gels, no differences were seen between the malignant hyperthermia susceptible and normal samples. Therefore, the samples were analyzed by SDS-PAGE, followed by immunoblotting with polyclonal antibodies against the calcium release channel protein. This methodology is more sensitive and specific than analysis by gel staining, and may therefore detect subtle differences in the protease digestion patterns not seen by gel staining alone. Four different concentrations of either trypsin, alpha-chymotrypsin or *Staphlyococcus aureus* protease V8 were used. No reproducible differences in malignant hyperthermia susceptible and normal samples were seen by immunostaining of the calcium release channel when either alpha-chymotrypsin or *Staphylococcus aureus* protease was used. However, as demonstrated in FIG. 2, when the samples were digested with trypsin, differences were detected in the staining pattern of the immunoblot. At a protease-protein ratio of 1:160 (6.25 ng/mg), the malignant hyperthermia susceptible sample contained an approximate 99 kDa band which was only a minor band in the normal sample, while the normal sample contained an 86 kDa band which was not detected in the malignant hyperthermia sample. These differences were not seen at lower trypsin concentrations (1.25 and 0.25 ng/mg), indicating that the differences in digestion of the malignant hyperthermia susceptible and normal calcium release channel may only be detectable over a limited range of trypsin concentrations.

Control experiments using antibodies against the sarcoplasmic reticulum ($Ca^{2+}+Mg^{2+}$)-ATPase, the junctional transverse tubular dihydropyridine receptor, and a junctional sarcoplasmic reticulum 94 kDa protein revealed no differences in the tryptic digestion pattern of malignant hyperthermia susceptible and normal sarcoplasmic reticulum. Immunopeptide maps of normal and malignant hyperthermia susceptible sarcoplasmic reticulum revealed differences only in the calcium release channel. One interpretation of these results is that the calcium release channel of malignant hyperthermia susceptible sarcoplasmic retriculum contains one or more trypsin susceptible peptide bonds which are either absent or less accessible in the calcium release channel of sarcoplasmic reticulum.

EXAMPLE II

Immunoblots of different preparations of malignant hyperthermia susceptible and normal sarcoplasmic reticulum digested with trypsin Skeletal muscle samples were treated with trypsin for 5 minutes at 37° C. as described in Example I and analyzed using a 5–16% SDS-PAGE. The ratio of sarcoplasmic reticulum to trypsin was 160:1. The immunoblot was stained with polyclonal sheep anti-rabbit calcium release channel antibodies followed by incubation with rabbit anti-sheep IgG conjugated to horseradish peroxidase.

Figure 3:
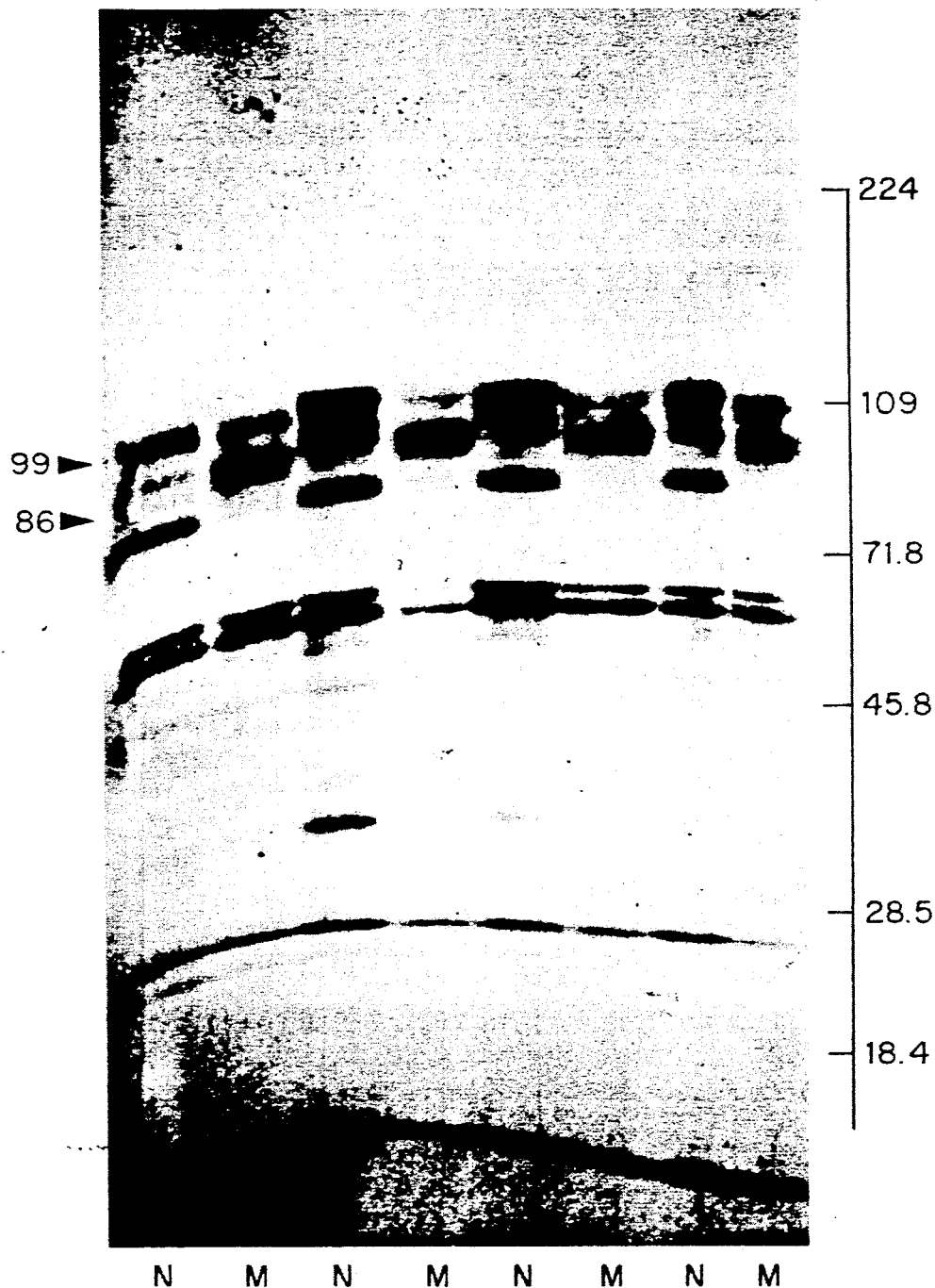
FIG. 3 is an immunoblot of different preparations of malignant hyperthermia susceptible and normal sarcoplasmic reticulum digested with trypsin.

Each lane in FIG. 3 contained 100 µg of either normal (N) or malignant hyperthermia susceptible (M) sarcoplasmic reticulum. The arrowheads on the left show the 86 kDa fragment which is detected in the normal sarcoplasmic reticulum but not in the malignant hyperthermia susceptible sarcoplasmic reticulum and the 99 kDa fragment which is prominent in the malignant hyperthermia susceptible sarcoplasmic reticulum. Molecular weight standards are indicated on the right.

To demonstrate consistent differences in the trypsin sensitivity of the malignant hyperthermia susceptible and normal release channel, four different preparations each of malignant hyperthermia susceptible and normal sarcoplasmic reticulum were treated with trypsin at a ratio of 160:1. Again, as can be seen in FIG. 3, more of the 99 kDa fragment is present in each of the malignant hyperthermia susceptible samples, while the 86 kDa fragment is seen in each of the normal samples. This experiment shows that the differences in digestion patterns between malignant hyperthermia samples and normal samples cannot be accounted for by pig-to-pig or preparation-to-preparation variability.

EXAMPLE III

Figure 4:
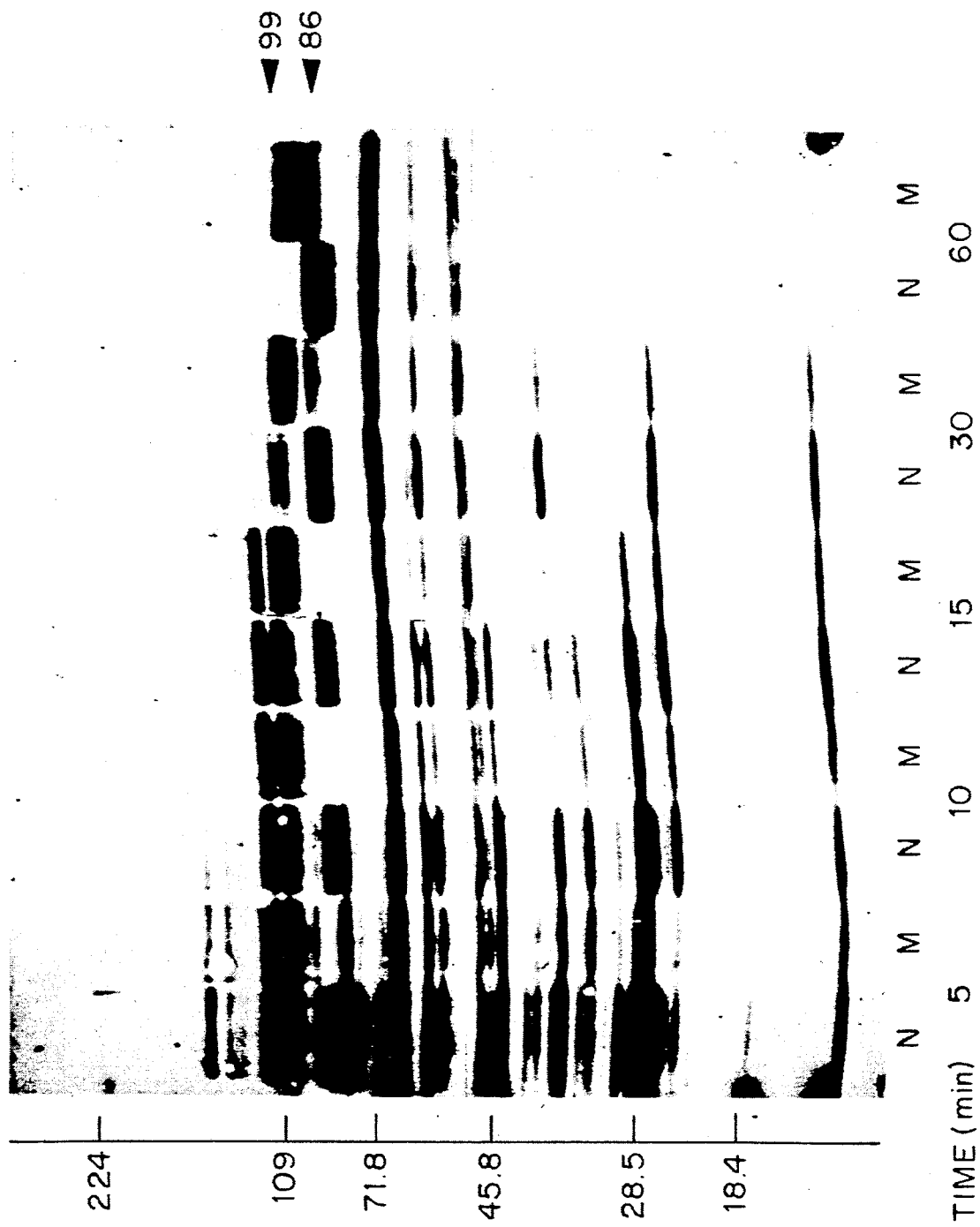
FIG. 4 is an immunoblot of a time course of trypsin digestion of malignant hyperthermia susceptible and normal sarcoplasmic reticulum.

Time course of trypsin digestion of malignant hyperthermia susceptible and normal sarcoplasmic reticulum Samples were treated with trypsin as described in Example I and analyzed using a 5–16% SDS-PAGE. The immunoblot was stained with sheep polyclonal anti-rabbit calcium release channel antibodies followed by incubation with rabbit anti-sheep IgG conjugated to horseradish peroxidase. Each lane of FIG. 4 contained 100 µg of either normal (N) or malignant hyperthermia susceptible (M) sarcoplasmic reticulum treated with 6.3 ng/µg sarcoplasmic reticulum or a ratio of 160:1 (sarcoplasmic reticulum:trypsin) at 30° C. The arrowheads on the right of FIG. 4 show the 86 kDa fragment which is detected in normal sarcoplasmic reticulum but not in malignant hyperthermia susceptible sarcoplasmic reticulum and the 99 kDa fragment which is prominent in the malignant hyperthermia susceptible sarcoplasmic reticulum. Molecular weight standards are indicated on the left of FIG. 4.

To explore further the nature of the differences in the pattern of trypsin digestion, malignant hyperthermia susceptible and normal samples were treated for various times at a trypsin:protein ratio of 1:160. Clear differences were seen, again, in immunostaining patterns of the malignant hyperthermia susceptible and normal calcium release channel peptides. However, this experiment shows that both malignant hyperthermia susceptible and normal samples contain a 99 kDa fragment at short incubation times (5-15 minutes). It is also demonstrated in FIG. 4 that while the 99 kDa normal fragment was almost completely absent by 30 minutes, the 99 kDa malignant hyperthermia susceptible fragment is only partially lost after 60 minutes of digestion. This is associated with the simultaneous appearance of an approximate 86 kDa fragment. Whether the 86 kDa immunostained band that is visible in the 30 and 60 minute malignant hyperthermia susceptible samples is the same as the 86 kDa band seen after 5 minutes of trypsin incubation with the normal sample remains to be determined. However, it is clear that the 86 kDa calcium release channel fragment is produced at very different times of trypsin incubation with malignant hyperthermia susceptible and normal sarcoplasmic reticulum.

EXAMPLE IV

Figure 5:
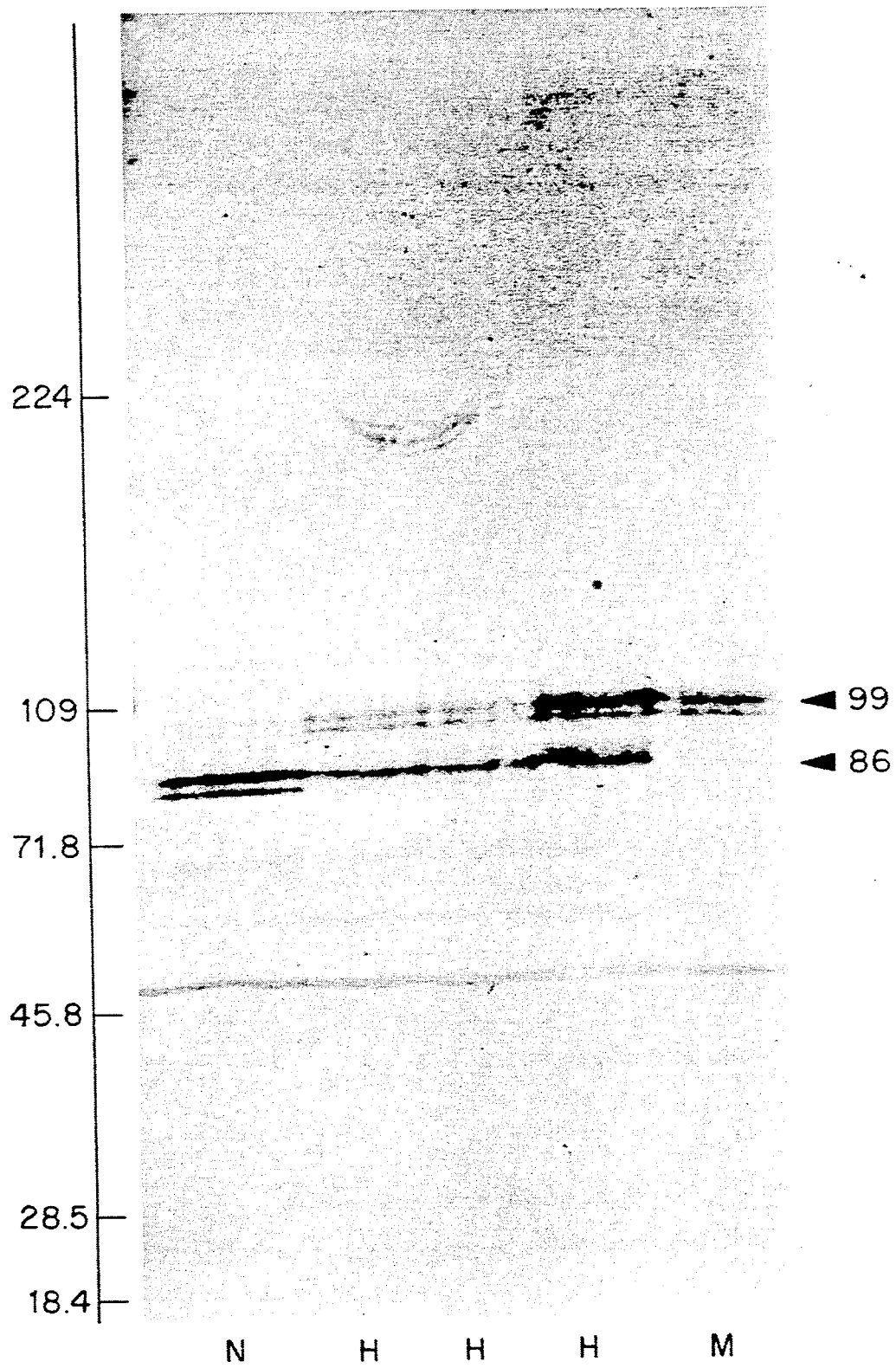
FIG. 5 is an immunoblot of malignant hyperthermia susceptible (M), heterozygote (H) and normal (N) sarcoplasmic reticulum digested with with trypsin at a ratio of 160:1 sarcoplasmic reticulum:trypsin.

Immunoblots of malignant hyperthermia susceptible (M), heterozygote (H), and normal (N) sarcoplasmic reticulum digested with trypsin Skeletal muscle samples were treated with trypsin as described in Example I for 5 minutes at 37° C., after which 75 μg per lane were analyzed on 3-12% SDS-PAGE. The nitrocellulose transfer was stained with polyclonal sheep anti-rabbit calcium release channel antibody followed by incubation with rabbit anti-sheep IgG conjugated to horseradish peroxidase. The arrowheads on the right of FIG. 5 show the 86 kDa fragment which is detected in the normal sarcoplasmic reticulum but not in the malignant hyperthermia susceptible and the 99 kDA fragment which is prominent in the malignant hyperthermia susceptible sarcoplasmic reticulum. Molecular weights are indicated on the left of FIG. 5.

In addition to the Yorkshire and the Pietrain pigs, which are homozygous normal and malignant hyperthermia susceptible, respectively, heterozygotes have been developed by crossbreeding of the two genotypes and backcrossing to Pietrains. The heterozygous pigs were found to be phenotypically non-malignant hyperthermia susceptible when challenged with halothane, consistent with the malignant hyperthermia susceptible gene being inherited in an autosomal recessive fashion. An advantage of these animals is that except for the halothane-sensitivity gene, most of the genes will be provided from the Pietrain breed. However, sarcoplasmic reticulum isolated from heterozygote displayed intermediate properties of calcium release and ryanodine binding activities when compared with the homozygous normal and homozygous malignant hyperthermia susceptible pigs. FIG. 5 illustrates the trypsin digestion pattern of the sarcoplasmic reticulum calcium release channel from 1 normal, 3 heterozygous and 1 malignant hyperthermia susceptible pig. Under conditions where the predominant malignant hyperthermia susceptible and normal fragments are 99 and 86 kDA, respectively, the heterozygous samples displayed both bands. Thus, the sarcoplasmic reticulum calcium release channel of heterozygous pigs demonstrates an intermediate pattern of trypsin digestion. This would be expected if the halothane sensitivity gene codes for the sarcoplasmic reticulum calcium release channel, i.e., pigs, heterozygous for the halothane-sensitivity gene contain one copy each of the normal and altered alleles of the sarcoplasmic reticulum calcium release channel gene. The results with the heterozygous also suggest that the differences in the immunopeptide maps of the malignant hyperthermia susceptible and normal sarcoplasmic reticulum calcium release channel are not due to other genes unrelated to malignant hyperthermia which may differ between the two breeds of pigs.

EQUIVALENTS

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. A method for diagnosing the malignant hyperthermia phenotype in a test sample from a pig, comprising the steps of:
    a) providing a test sample comprising isolated ryanodine receptor from skeletal muscle isolated from the pig;
    b) contacting the test sample with trypsin under conditions which result in the production of a protein transfer blot banding pattern in control samples isolated from a pig having the malignant hyperthermia phenotype and a pig having a normal phenotype, which banding pattern differs substantially in the relative intensity of a predetermined proteolytic fragment band when stained with anti-ryanodine receptor antibodies;
    c) separating the proteolytic digestion fragments from step b) on a gel by electrophoresis;
    d) transferring the proteolytic digestion fragments from the gel of step c) to a solid support thereby creating a protein transfer blot;
    e) contacting the protein transfer blot with polyclonal antibodies specifically reactive with the ryanodine receptor under conditions appropriate for the binding of the polyclonal antibodies with the ryanodine receptor;
    f) washing the protein transfer blot to remove non-specifically bound antibody;
    g) detecting the specific binding of the polyclonal antibodies to the proteolytic digestion fragments bound to the solid support;
    h) comparing the relative intensity of the predetermined proteolytic fragment band, if present, in the test sample with the intensity of the predetermined proteolytic fragment band in a control sample from a normal pig treated as described in steps b) through g) above, a substantial reduction in the relative intensity of the predetermined proteolytic fragment band in the test sample as compared with the predetermined proteolytic fragment band in the control sample, or the absence of said band, being characteristic of the malignant hyperthermia phenotype.

2. A method of claim 1 wherein the predetermined proteolytic fragment band migrates as a fragment having a molecular weight of about 86 kDa.

3. A method of diagnosing the malignant hyperthermia phenotype in a test sample from a pig, comprising the steps of:
    a) providing a test sample comprising sarcoplasmic reticulum isolated from skeletal muscle of the pig, the sarcoplasmic reticulum containing the ryanodine receptor;

b) contacting the test sample with trypsin under conditions which result in the production of a protein transfer blot banding pattern in a control sample isolated from a pig having the malignant hyperthermia phenotype and a pig having a normal phenotype, which banding pattern differs substantially in the relative intensity of a proteolytic fragment band which migrates as fragment having a molecular weight of about 86 kDa when stained with anti-ryanodine receptor antibodies,;

c) separating the proteolytic digestion fragments from step b) on a gel by electrophoresis;

d) transferring the proteolytic digestion fragments from the gel of step c) to a solid support thereby creating a protein transfer blot;

e) contacting the protein transfer blot with polyclonal antibodies specifically reactive with the ryanodine receptor under conditions appropriate for the binding of the polyclonal antibodies with the ryanodine receptor;

f) washing the protein transfer blot to remove non-specifically bound antibody;

g) detecting the specific binding of polyclonal antibodies to the ryanodine receptor proteolytic digestion fragments bound to the solid support;

h) comparing the relative intensity of the 86 kDa proteolytic fragment band in the test sample, if present, with the 86 kDa proteolytic fragment band in a control sample from a normal organism treated as described in steps b) through g) above, a substantial reduction in the intensity of the 86 kDa proteolytic fragment band in the test sample as compared with the same fragment in the control sample, or the absence of said band in the test sample, being characteristic of the malignant hyperthermia phenotype.

* * * * *